(12) United States Patent
Augusto et al.

(10) Patent No.: US 12,186,366 B2
(45) Date of Patent: Jan. 7, 2025

(54) CLUSTERIN FOR USE IN THE TREATMENT OF THROMBOTIC MICROANGIOPATHIES

(71) Applicants: UNIVERSITE DE BORDEAUX, Bordeaux (FR); CENTRE NATIONAL DE LA RECHERCHE SCIENTIFIQUE, Paris (FR); CENTRE HOSPITALIER UNIVERSITAIRE DE BORDEAUX, Talence (FR); INSERM—INSTITUT NATIONAL DE LA SANTE ET DE LA RECHERCHE MEDICALE, Paris (FR); UNIVERSITE D'ANGERS, Angers (FR); CENTRE HOSPITALIER UNIVERSITAIRE D'ANGERS, Angers (FR)

(72) Inventors: Jean-Francois Augusto, Soucelles (FR); Cecile Contin-Bordes, Merignac (FR); Yahsou Delmas, Merignac (FR); Patrick Blanco, Verdelais (FR); Yves Delneste, Bouchemaine (FR); Pascale Jeannin, Bouchemaine (FR); Celine Beauvillain, Les Hauts D'Anjou (FR)

(73) Assignees: UNIVERSITE DE BORDEAUX, Bordeaux (FR); CENTRE NATIONAL DE LA RECHERCHE SCIENTIFIQUE, Paris (FR); CENTRE HOSPITALIER UNIVERSITAIRE DE BORDEAUX, Talence (FR); INSERM—INSTITUT NATIONAL DE LA SANTE ET DE LA RECHERCHE MEDICALE, Paris (FR); UNIVERSITE D'ANGERS, Angers (FR); CENTRE HOSPITALIER UNIVERSITAIRE D'ANGERS, Angers (FR)

( * ) Notice: Subject to any disclaimer, the term of this patent is extended or adjusted under 35 U.S.C. 154(b) by 100 days.

(21) Appl. No.: 16/632,684

(22) PCT Filed: Jul. 20, 2018

(86) PCT No.: PCT/FR2018/051854
§ 371 (c)(1),
(2) Date: Jan. 21, 2020

(87) PCT Pub. No.: WO2019/016485
PCT Pub. Date: Jan. 24, 2019

(65) Prior Publication Data
US 2020/0138902 A1 May 7, 2020

(30) Foreign Application Priority Data
Jul. 21, 2017 (FR) .................... 1756912

(51) Int. Cl.
*A61K 38/17* (2006.01)
*A61P 9/10* (2006.01)
*G01N 33/92* (2006.01)

(52) U.S. Cl.
CPC ............ *A61K 38/1709* (2013.01); *A61P 9/10* (2018.01); *G01N 33/92* (2013.01); *G01N 2800/226* (2013.01)

(58) Field of Classification Search
CPC ............... A61K 2300/00; A61K 38/00; A61K 38/1709; A61K 9/0019; A61K 38/17;
(Continued)

(56) References Cited

U.S. PATENT DOCUMENTS

2015/0079613 A1* 3/2015 McKnight ............... A61P 43/00 435/7.92

FOREIGN PATENT DOCUMENTS

| WO | WO2001066689 A2 * | 9/2001 | |
|---|---|---|---|
| WO | WO2002022635 A1 * | 3/2002 | ............ C07H 21/02 |

(Continued)

OTHER PUBLICATIONS

Dabbs RA, Wilson MR (2014) Expression and Purification of Chaperone-Active Recombinant Clusterin. PLoS One. Jan. 23, 2014; 9(1): e86989. (Year: 2014).*
Clusterin preproprotein [*Homo sapiens*]. NP_001822.3 https://www.ncbi.nlm.nih.gov/protein/NP_001822.3 download [Aug. 14, 2020 3:50 :34 PM] (Year: 2020).*
Fuchs et al. Circulating DNA and myeloperoxidase indicate disease activity in patients with thrombotic microangiopathies. Blood (2012) 120 (6): 1157-1164. (Year: 2012).*
Cunin et al. Clusterin facilitates apoptotic cell clearance and prevents apoptotic cell-induced autoimmune responses. Cell Death and Disease (2016) 7, e2215. (Year: 2016).*

(Continued)

*Primary Examiner* — Melissa L Fisher
*Assistant Examiner* — Jia-Hai Lee
(74) *Attorney, Agent, or Firm* — CANTOR COLBURN LLP

(57) ABSTRACT

The present invention concerns clusterin for use in the treatment of thrombotic microangiopathies, and a pharmaceutical composition comprising clusterin for use in the treatment of thrombotic microangiopathies, said composition not comprising von Willebrand factor protease. The present invention also concerns an ex vivo method for stratifying a patient suffering, or likely to be suffering, from TMA, comprising the following steps: 1) measuring, in a biological sample from said patient, the amount $L_C$ of clusterin, and 2) comparing the amount $L_C$ measured in step 1) with an amount $L_{ref}$ of clusterin by calculating the score $S1=L_C/L_{ref}$, in which: •If $S1 \leq 1$, the patient is considered to be likely to benefit from a treatment of the TMA with clusterin, •If $S1 > 1$, the patient is not considered to be likely to benefit from treatment of TMA with clusterin.

7 Claims, 8 Drawing Sheets
Specification includes a Sequence Listing.

(58) Field of Classification Search
CPC .......... A61K 38/16; A61P 37/02; A61P 37/00; A61P 7/00; A61P 9/10; C07K 2317/21; C07K 14/47; C07K 14/435; C12Q 2600/156; G01N 2800/52; G01N 33/6893; G01N 2333/775
See application file for complete search history.

(56) References Cited

FOREIGN PATENT DOCUMENTS

| WO | 0242441 A2 | 5/2002 |
|---|---|---|
| WO | 2013188686 A2 | 12/2013 |
| WO | 2014035876 A1 | 3/2014 |
| WO | 2016176565 A1 | 11/2016 |

OTHER PUBLICATIONS

Stahl et al. A novel mutation in the complement regulator clusterin in recurrent hemolytic uremic syndrome. Molecular Immunology 46 (2009) 2236-2243. (Year: 2009).*

Benz et al.; "Thrombotic microangiopathy: new insights"; Current Opinion in Nephrology and Hypertension, vol. 19, Issue No. 3; 2010; pp. 242-247.

Cofiell et al.; "Eculizumab reduces complement activation, inflammation, endothelial damage, thrombosis, and renal injury markers in aHUS"; Blood, vol. 125, Issue No. 21; 2015; pp. 3253-3262.

Craggs et al.; "Clusterin/Apolipoprotein J immunoreactivity is associated with white matter damage in cerebral small vessel diseases"; Neuropathology and Applied Neurobiology, vol. 42, Issue No. 2; 2016; pp. 194-209.

Cunin et al.; "Clusterin facilitates apoptotic cell clearance and prevents apoptotic cell-induced autoimmune responses"; Cell Death and Disease, vol. 7, Issue No. 5; 2016; e2215 doi:10.1038/cddis.2016.113.

International Search Report and Written Opinion for International Application No. PCT/FR2018/051854; International Filing Date: Jul. 20, 2018; Date of Mailing: Oct. 23, 2018; 12 pages.

Kazue; "Terminal complement complex (TCC) levels in urine in patients with renal diseases"; The Hokkaido Journal of Medical Science, vol. 76, Issue No. 2; 2001; pp. 71-84.

Lankford et al.; "Thrombotic Thrombocytopeniarpura: New Insights in Disease Pathogenesis and Therapy"; Transfusion Medicine Reviews, vol. 14, Issue No. 3; 2000; pp. 244-257.

* cited by examiner

SEQUENCE LISTING

<160> NUMBER OF SEQ ID NOS: 1

<210> SEQ ID NO 1
<211> LENGTH: 449
<212> TYPE: PRT
<213> ORGANISM: Homo sapiens

<400> SEQUENCE: 1

Met Met Lys Thr Leu Leu Phe Val Gly Leu Leu Leu Thr Trp Glu
1               5                   10                  15

Ser Gly Gln Val Leu Gly Asp Gln Thr Val Ser Asp Asn Glu Leu Gln
            20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
            115                 120                 125

Cys Arg Ser Gly Ser Gly Leu Val Gly Arg Gln Leu Glu Glu Phe Leu
        130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
            195                 200                 205

Phe Ser Leu Pro His Arg Arg Pro His Phe Phe Pro Lys Ser Arg
        210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
            275                 280                 285

Arg His Asn Ser Thr Gly Cys Leu Arg Met Lys Asp Gln Cys Asp Lys
        290                 295                 300

Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
                325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
            355                 360                 365

-continued

```
Val Ser Arg Leu Ala Asn Leu Thr Gln Gly Glu Asp Gln Tyr Tyr Leu
    370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
            405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
        435                 440                 445

Glu
```

CLUSTERIN FOR USE IN THE TREATMENT OF THROMBOTIC MICROANGIOPATHIES

CROSS REFERENCE TO RELATED APPLICATIONS

This application is a National Stage application of PCT/FR2018/051854, filed on Jul. 20, 2018, which claims the benefit of French Application No. FR 1756912, filed on Jul. 21, 2017, both of which are incorporated by reference in their entirety herein.

TECHNICAL FIELD

The present invention relates to the use of a protein for use in the treatment of thrombotic microangiopathies, and also to an ex vivo method for stratification of a patient who is or may be suffering from TMA.

In the description below, the references between square brackets ([ ]) refer to the list of references present at the end of the text.

PRIOR ART

The name thrombotic microangiopathy (TMA) groups together a set of rare diseases characterized by the occurrence of endothelial lesions which result in small-caliber vessel occlusion by thrombosis and the consequence of which is tissue ischemia. Tissue ischemia is responsible for cell destruction and for the release into the extracellular medium by the dying cells of molecules that are normally confined within the cell. These danger molecules are pro-inflammatory and have a cytotoxic action on the cells of the host. Recent data identify histones (in free form or complexed with DNA) as danger molecules, the role of which is essential during TMAs.

TMAs are pathological conditions which involve the vital prognosis, the kidney and the brain being the target organs most frequently affected. The most conventional forms of TMA are thrombotic thrombocytopenic purpura (TTP), and hemolytic uremic syndrome (HUS), which may be either associated with bacteria, or not associated with bacteria. HUS associated with bacteria is the most frequent form of HUS (90% of HUS); several strains of bacteria (*Escherichia coli* O157:H7; *Shigella*, pneumococci, *Escherichia coli* O104 in particular) are currently known to cause the disease by secreting a toxin known as shiga toxin. HUS not associated with bacteria represents approximately 10% of HUS, where it is frequently found in the context of genetic susceptibility.

The number of new cases of TTP is from 5 to 10 cases per million inhabitants and per year. HUS frequency is also very close to these values.

TMAs include, in addition to these most conventional forms, HELLP syndrome, which is a serious complication or a variant of pre-eclampsia in pregnant women, characterized by hemolysis, elevated liver enzymes and a low platelet count. Secondary forms of TMA also exist which occur in a specific context such as, for example, during certain treatments, during chemotherapy, during cancer or during a bone marrow allograft.

The current treatment of the most conventional forms is generally carried out by plasma exchanges at the beginning of the treatment, with the exception of shiga toxin-associated HUS occurring in children. The aim of the plasma exchanges is to provide large volumes of plasma from volunteer donors and which contain the ADAMTS13 protein (in TTP) or complement proteins (in HUS). Other treatments are often combined therewith, in particular corticosteroids. When they are efficacious, the plasma exchanges are continued until long-lasting normalization of the platelet count is obtained (at least 48 hours), then they are gradually spaced out. However, in many cases, plasma exchanges prove to be of little efficacy.

In situations where the response to standard treatment is not optimal, supplementary treatments are added. The treatment most commonly used in this context, an anti-CD20 antibody (Rituximab), aims to combat the antibody production by the patient by transiently destroying the B lymphocytes. It is usually used in the context of therapeutic protocols and in consultation with the reference center.

In patients suffering from idiopathic HUS, referred to as atypical, the treatment comprises medicaments capable of blocking the complement proteins responsible for the disease. Eculizumab is currently the only treatment authorized in the atypical HUS indication. This treatment is extremely expensive since a bottle of 300 mg of Eculizumab costs more than 4000 euros and, as maintenance treatment, the dosage regimen is 1200 mg per 14 days.

Although often efficacious, these treatments have a delayed action time which is variable between individuals and depending on the nature of the TMA. However, the etiological diagnosis can take several days/weeks. Thus, taking TTP as example, mortality currently remains approximately 15%.

There is thus a real need for new treatments, which overcome these faults, drawbacks and obstacles of the prior art, in particular which act more rapidly and regardless of the etiology of the disease, in order to make it possible to reduce the mortality of the acute phase of TMAs which is mainly early.

DESCRIPTION OF THE INVENTION

After considerable research, the inventors have managed to solve this technical problem.

Surprisingly, the inventors have shown that clusterin binds to histones and that it inhibits the inflammatory and cytotoxic action thereof.

The inventors have in fact shown that clusterin binds to histones, which are danger molecules with a central role in TMAs. They have also shown that clusterin neutralizes the actions of histones, firstly by blocking the production of pro-inflammatory molecules, in particular of pro-inflammatory cytokines such as IL-6 and TNFα, by human monocytes, and secondly by blocking the induction of endothelial cell death, in particular by neutralizing the capacity of histones to induce endothelial cell death. The inventors have also shown that the addition of clusterin to sera from patients containing histones decreases their toxicity with respect to endothelial cells.

Furthermore, the inventors have shown that the amount of clusterin correlates with the state of health of patients suffering from TMA. They have in fact been able to demonstrate that serum clusterin levels are lower in patients suffering from TMA at diagnosis than in healthy subjects.

The invention could facilitate the treatment of TMAs for which the current treatments depend on the etiology. The use of clusterin could thus be proposed to any patient with TMA regardless of the etiology, allowing a faster treatment that is not dependent on the etiological diagnosis.

Thus, a first subject relates to clusterin for use thereof in the treatment of thrombotic microangiopathies.

Clusterin (Clu), also known as apolipoprotein J, is an 80 kDa soluble heterodimeric glycoprotein bonded by disulfide bridges, which is strongly conserved during evolution and among mammals. Clusterin is abundant in physiological fluids (at concentrations ranging from 100 to 300 µg/ml in human serum by way of example) and is induced in response to a large variety of cell and tissue lesions. It is known that clusterin has a chaperone activity and is a functional homolog of the intracellular small heat shock proteins (HSPs). It binds to the hydrophobic domains of non-native proteins and targets them for receptor-mediated internalization and intracellular lysosomal degradation. This function allows clusterin to interact with a wide spectrum of molecules, such as lipids, complement system components, amyloid plaque-forming proteins, and immunoglobulins.

In the context of the present invention, the term "clusterin" has its general meaning, and denotes a glycoprotein as described above. The clusterin may be an animal clusterin or a human clusterin. It may be a clusterin chosen from the group comprising a plasma clusterin, a recombinant clusterin and a synthetic clusterin.

Plasma clusterin can be obtained by purification from plasma, in particular human plasma, by any purification method known to those skilled in the art, for example by means of immunoaffinity, of cation exchange, of plasma fractionation and/or of size exclusion chromatography.

Recombinant clusterin can be obtained by standard recombinant DNA techniques, well known to those skilled in the art. For example, a gene encoding a clusterin can be introduced by means of a vector into the genome of a producer species, such as a bacterium, a mammalian cell in culture or a transgenic animal. The vectors which allow the introduction, maintenance and expression of genes in a host cell are known to those skilled in the art. Generally, they have sequences essential to the expression of the gene introduced, such as promoter sequences, polyadenylation sequences and selectable genes. Such vectors can be chosen from the ones known to those skilled in the art, for example from adenoviruses, retroviruses, plasmids or bacteriophages, this list not being limiting. Any mammalian cell can be used as host cell, that is to say as cell expressing the gene encoding clusterin, for example CHO, CHO dhfr– (for example CHO DX BII, CHO DG44), CHO Lec13, YB2/0, SP2/0, NSO, 293, BHK, Jurkat, Vero or COS.

Synthetic clusterin can be obtained by any known method of de novo protein design other than that used to prepare recombinant protein, such as for example by assembly on a matrix.

Regardless of the method of preparation of the clusterin, the clusterin sequences from numerous species are known and can be used in the context of the invention. For example, the amino acid sequence of clusterin may be that of the sequence SEQ ID No.: 1.

```
Clusterin_homo sapiens
                                          SEQ ID NO: 1
MMKTLLLFVG LLLTWESGQV LGDQTVSDNE LQEMSNQGSK

YVNKEIQNAV NGVKQIKTLI EKTNEERKTL LSNLEEAKKK

KEDALNETRE SETKLKELPG VCNETMMALW EECKPCLKQT

CMKFYARVCR SGSGLVGRQL EEFLNQSSPF YFWMNGDRID

SLLENDRQQT HMLDVMQDHF SRASSIIDEL FQDRFFTREP

QDTYHYLPFS LPHRRPHFFF PKSRIVRSLM PFSPYEPLNF
```
-continued
```
HAMFQPFLEM IHEAQQAMDI HFHSPAFQHP PTEFIREGDD

DRTVCREIRH NSTGCLRMKD QCDKCREILS VDCSTNNPSQ

AKLRRELDES LQVAERLTRK YNELLKSYQW KMLNTSSLLE

QLNEQFMWVS RLANLTQGED QYYLRVTTVA SHTSDSDVPS

GVTEVVVKLF DSDPITVTVP VEVSRKNPKF METVAEKALQ

EYRKKHREE
```

The clusterin used may be a variant having at least 70% identity with the sequence SEQ ID No.: 1, for example 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or 100% identity with the sequence SEQ ID No.: 1. The sequence identity can be determined by means of any suitable technique known to those skilled in the art, for example by means of a sequence alignment algorithm such as BLAST P. In particular, a clusterin variant may be a variant of which the function is conserved. In this respect, it may be a clusterin in which a given amino acid residue in natural clusterin is modified in the variant without impairing either the conformation or the overall function of the clusterin, including, but not being limited to, the replacement of an amino acid with an amino acid having similar properties, such as for example the polarity, the hydrogen-bonding potential, the hydrophobicity, the acidity, the basicity, the aromaticity, etc. Consequently, a variant also denotes a polypeptide which has at least 70% amino acid identity and which has the same properties or functions that are identical or substantially similar to the native or parental protein to which it is compared.

Without wishing to be bound by a mechanism of action, it appears that the action of clusterin is linked to the chaperone function of the histones of said clusterin.

As used herein, the term "histone" has its general meaning. Histones are small basic proteins with a high lysine or arginine content, the function of which is in DNA packaging. Histones are highly conserved and can be grouped together in five major classes: H1/H5, H2A, H2B, H3 and H4 organized in two super-classes of core histones (H2A, H2B, H3 and H4) and linker histones (H1 and H5). In the context of the invention, a histone protein may be a full-length histone, a fragment or a variant thereof. A histone variant may be modified for example by amino acid deletion, addition and/or substitution. Alternatively, a histone may be modified by acetylation and/or methylation of the lysine and of the arginine. In general, the modifications do not substantially compromise the polycationic nature of the histone or the capacity of the histone to localize in an organ.

Advantageously, clusterin binds to histones so as to inhibit all or part of the inflammatory and/or toxic action thereof. It may involve an inhibition of at least 20%, for example 30%, or 40%, or 50%, or 60%, or 70%, or 80%, or 90%, or 100%, of the inflammatory and/or toxic action of histones.

Advantageously, clusterin blocks the production of pro-inflammatory molecules, in particular pro-inflammatory cytokines such as IL-6 and TNFα, by human monocytes. This may involve the blocking of at least 20%, for example 30%, or 40%, or 50%, or 60%, or 70%, or 80%, or 90%, or 100%, of the production of pro-inflammatory molecules.

Advantageously, clusterin blocks the induction of endothelial cell death, in particular by neutralizing the capacity of histones to induce endothelial cell death. This may involve the blocking of at least 20%, for example 30%, or 40%, or 50%, or 60%, or 70%, or 80%, or 90%, or 100%, of the induction of endothelial cell death.

In the context of the invention, all or some of the effects mentioned above may take place.

The thrombotic microangiopathies may be chosen from thrombotic thrombocytopenic purpura (TTP), hemolytic uremic syndrome (HUS) associated or not associated with bacteria, HELLP syndrome and secondary forms of TMA, for example those occurring during certain treatments, during chemotherapy, during cancer or during a bone marrow allograft.

For the purposes of the present invention, the term "treatment" is intended to mean the administration of clusterin to a subject either presenting one or more symptoms of a TMA, or diagnosed with a TMA without presenting TMA symptoms, for example diagnosed at an early stage of TMA. Advantageously, the treatment can be administered for treating any TMA, that is to say whether it is HUS, TTP, HELLP syndrome or secondary TMA, without the type of TMA having necessarily been predetermined. This has the advantage of making it possible to treat patients without waiting to have defined the TMA subtype, and thus avoiding worsening of the disease, and/or the appearance of symptoms. Alternatively, the treatment can be administered after assaying of the clusterin, this assaying making it possible to stratify the patients and optionally to propose the treatment only to patients having low clusterin levels, which is a marker for the severity of the disease.

Advantageously, the treatment can be an improvement or a disappearance of one or more symptoms of the TMA, or a stabilization of all or some of the symptoms of the TMA, or a slowing down of the progression of all or some of the symptoms of the TMA.

The treatment can be carried out by administration of a therapeutically effective dose of clusterin, which is a minimum dose that makes it possible to confer the therapeutic benefit on a patient. It may be a dose determined by the physician according to the pathological condition, the stage of the pathological condition, the initial assay of the amount of clusterin of the patient, and/or the patient. For example, the daily clusterin dose may be between 0.01 and 1000 mg per adult per day. It may for example be a daily dose of 0.01, 0.05, 0.1, 0.5, 1.0, 2.5, 5.0, 10.0, 15.0, 25.0, 50.0, 100, 250 or 500 mg of clusterin. The dosage may be adjusted according to the stage of treatment, for example it may be increased or decreased during treatment depending on the observations of the physician.

The treatment may be administered by any suitable route of administration. It may for example be an oral administration or a parenteral administration of clusterin. In the case of a parenteral administration, it may for example be an intravenous administration, an intramuscular administration or a subcutaneous administration.

Advantageously, the clusterin can be administered as described above, in combination with at least one other active ingredient or treatment known in the treatment of TMAs. In the case of TTP, it may be a treatment chosen from plasma exchanges, corticotherapy, immunosuppressants, an anti-CD20, such as for example Rituximab, a monoclonal antibody directed against von Willebrand factor, such as Caplacizumab. In the case of typical HUS, it may be at least one treatment chosen from a symptomatic treatment, plasma exchanges, a monoclonal antibody directed against the complement C5 fraction, such as for example Eculizumab, and an anti-CD20, such as for example Rituximab. In the case of atypical HUS, it may be at least one treatment chosen from plasma exchanges and a monoclonal antibody directed against the complement C5 fraction, such as Eculizumab. In the case of HELLP syndrome, it may be at least one treatment chosen from transfusion and an induced birth if the condition of the patent worsens.

Another subject of the invention relates to a pharmaceutical composition comprising clusterin, for use thereof in the treatment of thrombotic microangiopathies, said composition not comprising von Willebrand factor protease, ADAMTS13.

In particular, the pharmaceutical composition of the invention may be used in the treatment of HUS and of HELLP syndrome.

The clusterin is as described above.

The pharmaceutical composition may comprise approximately 0.01 mg to approximately 1000 mg of clusterin, for example from approximately 1 mg to approximately 100 mg. An effective dose of clusterin is generally given at a dose of approximately 0.0002 mg/kg to approximately 20 mg/kg of body weight per day, more particularly from approximately 0.001 mg/kg to 7 mg/kg of body weight per day.

Typically, the pharmaceutical composition may comprise, in addition to clusterin, one or more pharmaceutically acceptable excipients, and optionally at least one sustained-release matrix, such as biodegradable polymers.

The terms "pharmaceutical" and "pharmaceutically acceptable" refer to molecular entities or compositions, the quality of which meets the requirements of the standards in force. A pharmaceutically acceptable carrier or excipient refers to a bulking agent, a diluent, an encapsulation material or a formulation adjuvant, which is semi-solid or liquid and nontoxic, of any suitable type. In the pharmaceutical composition of the present invention for oral, sublingual, subcutaneous, intramuscular, intravenous, transdermal, local or rectal administration, the clusterin, alone or in combination with another active ingredient, may be administered in a unit administration form, optionally as a mixture with conventional pharmaceutical carriers, to animals and human beings.

The suitable unit administration forms comprise oral administration forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal, intraarterial and intranasal administration forms, and rectal administration forms. Generally, the pharmaceutical composition may contain carriers, which are pharmaceutically acceptable for an injectable formulation. Said carriers may in particular be isotonic, sterile, saline solutions (such as monosodium or disodium phosphate, sodium, potassium, calcium or magnesium chloride and the like or mixtures of such salts), or dry compositions, in particular freeze-dried compositions, which, by addition, as appropriate, of sterilized water or of physiological saline solution, enable the formation of injectable solutions. The pharmaceutical forms suitable for an injectable use comprise sterile aqueous solutions or dispersions, formulations including sesame oil, groundnut oil or an aqueous propylene glycol, and sterile powders for the extemporaneous preparation of sterile injectable solutions or dispersions. In any event, the formulation must be sterile and fluid so that it can be injected using a syringe. It must be stable under the conventional production and storage conditions and must be stable in order to prevent contamination by microorganisms, such as bacteria and fungi. Solutions comprising compounds of the invention as free base or pharmacologically acceptable salts can be prepared in water in an appropriate manner, optionally with a surfactant, such as hydroxypropylcellulose. The dispersions can also be prepared in a medium of glycerol, liquid polyethylene glycols and mixtures thereof and in oils. Under normal storage and use conditions, these preparations may contain a preservative in order to prevent microorganism growth. The clusterin can be formulated in a neutral form or in the form of a salt.

The pharmaceutically acceptable salts comprise the acid addition salts (formed with the free amino groups of the protein), which addition salts are formed with inorganic acids, such as, for example, hydrochloric acid or phosphoric acid, or organic acids such as acetic acid, oxalic acid, tartaric acid or mandelic acid. The salts formed with the free carboxyl groups may also be derived from inorganic bases such as, for example, sodium, potassium, ammonium, calcium or ferric hydroxides, and organic bases such as isopropylamine, trimethylamine, histidine and procaine. The support may also be a solvent or a dispersion medium containing, for example, water, ethanol, polyol (for example glycerol, propylene glycol and liquid polyethylene glycol, etc.), suitable mixtures thereof and plant oils. The suitable fluidity can be maintained, for example, by using a coating, such as lecithin, by maintaining the required particle size in the case of the dispersion, and by using surfactants. The action of the microorganisms can be prevented by addition of antibacterial and antifungal agent, for example parabens, chlorobutanol, phenol, sorbic acid or thimerosal. Optionally, it may be preferable to include isotonic agents, for example sugars or sodium chloride. Prolonged absorption of the injectable compositions can be brought about by using, in the composition, absorption-delaying agents, for example aluminum monostearate and gelatin. Sterile injectable solutions can be prepared by incorporating the active compounds in the required amount in the appropriate solvent with several of the other ingredients listed above, as required, followed by filtration sterilization. Generally, the dispersions can be prepared by incorporating the various sterilized active ingredients in a sterile carrier which contains the basic dispersion medium and the other possible ingredients listed above. In the case of sterile powders for the preparation of sterile injectable solutions, the preferred preparation methods are vacuum-drying and freeze-drying techniques, which produce a powder of the active ingredient plus any additional desired ingredient starting from a previously filtration-sterilized solution thereof. For parenteral administration in an aqueous solution, for example, the solution may be suitably buffered if required and the liquid diluent may be first made isotonic with a sufficient amount of saline solution or of glucose. These aqueous solutions are particularly suitable for intravenous, intramuscular, subcutaneous and intraperitoneal administrations.

Another subject of the invention relates to an ex vivo method for stratification of a patient who is or who may be suffering from TMA, comprising the following steps:
1) measuring, in the biological sample from said patient, the clusterin level $L_C$, and
2) comparing the level $L_C$ measured in step 1) with a reference clusterin level $L_{ref}$ by calculating the score $S1=L_C/L_{ref}$,
wherein:
if $S1 \leq 1$, the patient is considered to be liable to receive a benefit from a TMA treatment with clusterin,
if $S1 > 1$, the patient is not considered to be liable to receive a benefit from a TMA treatment with clusterin.

For the purposes of the present invention, the term "stratification" is intended to mean the therapeutic approach wherein the objective is to select patients who should be administered a treatment as a function of a predictive marker, in the case in point clusterin, in order to treat only the subpopulation for whom the treatment is liable to provide a benefit among those diagnosed with a TMA.

The stratification method of the invention can thus be carried out upstream of a clusterin treatment given to patients diagnosed with a TMA, in order to target a population most liable to receive a benefit from the treatment. Indeed, the inventors have shown that patients who present low clusterin levels at the time of diagnosis of the TMA, in particular less than or equal to 200 µg/ml, also have lower platelet levels and higher LDH levels, which are two markers of the severity, at least in terms of hematology, of the disease.

For the purposes of the present invention, the term "biological sample" is intended to mean any biological sample obtained from a subject, in particular already diagnosed or in the process of being diagnosed with a TMA. The sample must be liable to contain clusterin. The sample may for example be a body fluid, which may or may not contain cells, for example blood, whether it is serum and/or plasma, urine, saliva or a biopsy. It may also be a tissue section, such as frozen sections taken for histological purposes. The term "biological sample" also encompasses any material derived from a biological sample, for example the cells (or their progeny) isolated from the sample, or proteins extracted from the sample. The treatment of a biological example can involve one or more steps chosen from filtration, distillation, extraction, concentration, inactivation of interfering components or addition of reagents. When the biological sample is a blood sample, it may be whole blood, serum or plasma.

The step of measuring, in the biological sample from the patient, the clusterin level $L_C$ can be carried out by any suitable method known to those skilled in the art. The clusterin measured may be free clusterin or complexed clusterin. This step can for example comprise bringing the sample into contact with one or more binding partners capable of selectively interacting with the clusterin contained in the biological sample. A binding partner may be an antibody, such as monoclonal antibodies or aptamers. Solid supports that can be used in the implementation of this step may be for example substrates such as nitrocellulose (for example, in membrane or microtitration form), polyvinyl chloride (for example, microtitration wells or sheets), polystyrene latex (for example, microtitration beads or plates), polyvinylidene fluoride, diazotized paper, nylon membranes, activated beads, or magnetically reactive beads, this list not being limiting. The clusterin may also be revealed with a second binding partner, such as a clusterin-specific antibody or aptamer. As a general rule, the second binding partner is a specific antibody conjugated to an enzyme. The amount of clusterin can be measured using standard immunodiagnostic techniques, including immunoassays such as competition, direct reaction or sandwich assays. Such assays comprise, without being limited thereto, agglutination assays, enzyme-mediated immunoassays, such as ELISA, assays of the biotin/avidin type, radioimmunoassays, immunoelectrophoresis or immunoprecipitation. The assay may for example be the Human Clusterin ELISA Kit assay, Thermo Scientific™ Pierce™ sold by Invitrogen or a Quantikine® ELISA assay—R&D Systems, specific for assaying in serum and human plasma.

The predetermined reference value $L_{ref}$ may relate to a value derived from population studies, including, without limitation, subjects from the same age group or from a similar age group, subjects belonging to the same ethnic group or a similar ethnic group, and subjects having the same degree of severity of the disease. Such predetermined reference values may be derived from statistical analyses and/or from population risk prediction data obtained from mathematical algorithms and indices calculated for the disease. For example, the predetermined reference value may be derived from the amount of clusterin in a control sample from one or more subjects not suffering from TMA. Alternatively, a retrospective measurement of the amount of clusterin in samples from subjects who were historically correctly classified may be used to establish the predetermined reference value.

For the purposes of the present invention, the expression "benefit from a TMA treatment" is intended to mean an improvement or a disappearance of one or more symptoms of the TMA, or a stabilization of all or some of the symptoms of the TMA, or slowing down of the progression of all or some of the symptoms of the TMA.

For example, for the determination of the reference value, the amount of clusterin can be measured in 100 biological samples from 100 subjects. Once the first two subsets have been separated, Kaplan Meier curves are constructed for each of the two subsets, and the p value between the two subsets can be calculated. The reference value is then selected in such a way that the distinction on the basis of the minimum p value criterion is the strongest. In other words, the amount of clusterin corresponding to the limit between the two subsets for which the p value is the minimum is considered to be the predetermined reference value. It should be noted that the predetermined reference value is not necessarily the median value of the amount of clusterin.

Thus, the predetermined reference value allows a distinction between a patient who may be considered to be liable to receive a benefit from a TMA treatment with clusterin, and a patient who may be considered to be not liable to receive a benefit from a TMA treatment with clusterin.

Other advantages may further appear to those skilled in the art on reading the examples below, illustrated by the appended figures, and given by way of illustration.

EXAMPLES

Example 1: Clusterin Neutralizes the Actions of Histones by Blocking the Production of Pro-Inflammatory Molecules Human monocytes were isolated from the blood of healthy donors by magnetic sorting (positive sorting on the basis of expression of the CD14 marker CD14; Miltenyi Biotech, Bergisch Gladbach, Germany). The monocytes ($2 \times 10^6$ cells/ml) were incubated for 12 h with 12.5 µg/ml of histones (Sigma), in the presence or absence of 25 µg/ml of clusterin (CLU). The IL-6 was quantified by ELISA (Diaclone, Besançon, France) in the culture supernatants. The results are expressed in pg/ml (mean±SD, n=6).

Figure 1:
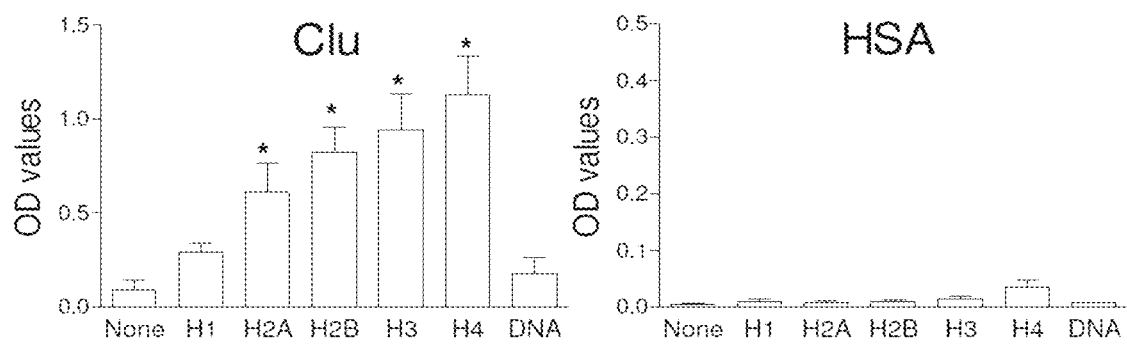
FIG. 1 represents the clusterin binding to histones. Histones H1, H2A, H2B, H3 and H4 (New England Biolabs, Ipswich, MA) or genomic DNA from human cells, were immobilized at the bottom of ELISA plates (1 μg/ml) in 10 mM carbonate/bicarbonate buffer, pH=9.6. After saturation, the plates were incubated with 1 μg/ml of recombinant human clusterin (R&D Systems, Abingdon, UK) or of human serum albumin (HSA; Sigma, St Louis, MO), coupled to biotin. The binding of Clu or of HSA to the histones was demonstrated with peroxidase-coupled streptavidin. The results are expressed as optical density (mean±SD, n=5). The HSA molecule was used as control protein. The binding of the genomic DNA in the ELISA plates was verified with a peroxidase-coupled anti-DNA antibody (data not shown).
Figure 2:
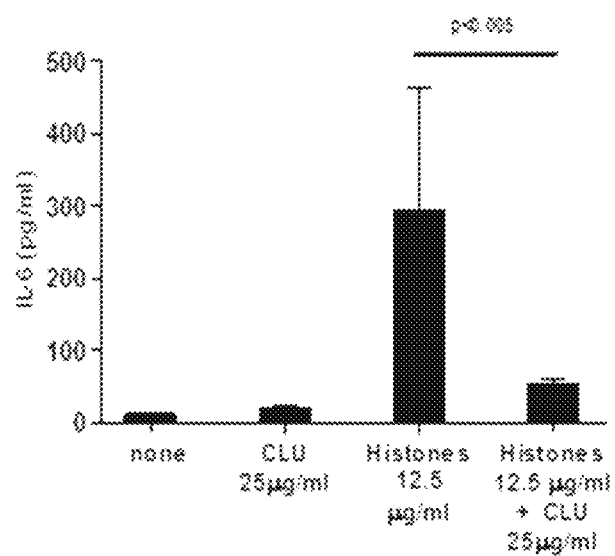
FIG. 2 represents the ELISA quantification of IL-6, in pg/ml, in the culture supernatants of human monocytes isolated from the blood of healthy donors by magnetic sorting then incubated for 12 h with 12.5 μg/ml of histones, in the presence (diagram 4) or in the absence (diagram 3) of 25 μg/ml of clusterin (CLU). Diagram 1 is the control of the culture of monocytes alone, and diagram 2 is the control of the culture of monocytes incubated with 25 μg/ml of clusterin.

The results are shown in FIG. 2.

Example 2: Clusterin Protects the Endothelial Cells Against Death Induced by Histone-Containing Sera Human endothelial cells (HDMECs from Promocell) are incubated for 15 min either in the presence of control sera (HNS; idem) in the presence or absence of histones (50 ng/ml Histones from Roche), or with patient sera containing endogenous histones (SS; n=5, 10% vol/vol) in the presence or absence of 200 ng/ml of Clu. After 15 min, the endothelial cells are labeled with annexin V and propidium iodide (Becton Dickinson kit) in order to evaluate the percentage of apoptotic cells by flow cytometry.

Figure 3:
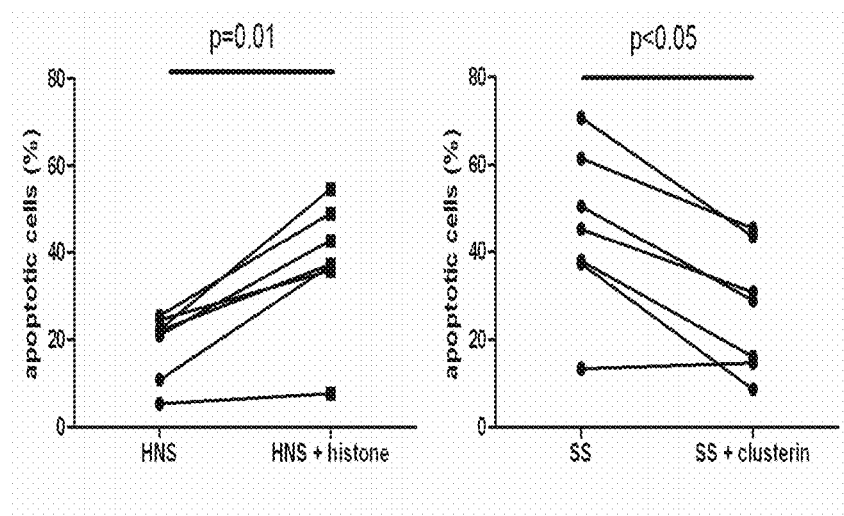
FIG. 3 represents the percentage of apoptotic cells measured in the case of human endothelial cells incubated for 15 min either (1) left-hand graph: in the presence of control sera (HNS) in the presence or absence of histones (50 ng/ml) (Histones from Roche), or (2) right-hand graph: with sera from patients containing endogenous histones (SS; n=5, 10% vol/vol) in the presence or absence of 200 ng/ml of Clu.

The results are shown in FIG. 3.

Example 3: The Amount of Clusterin is Associated with the Activity of the TMA The serum clusterin levels are lower in the patients suffering from TMA at diagnosis than in the healthy subjects. The serum clusterin level was assayed in 11/14 patients at the time of the $3^{rd}$ month after TMA diagnosis, after treatment. It did not differ significantly from that of the population of healthy subjects, but was significantly higher than at diagnosis. The clusterin was assayed by ELISA (R&D Systems) in sera from healthy subjects and from patients suffering from TMA.

Figure 4:
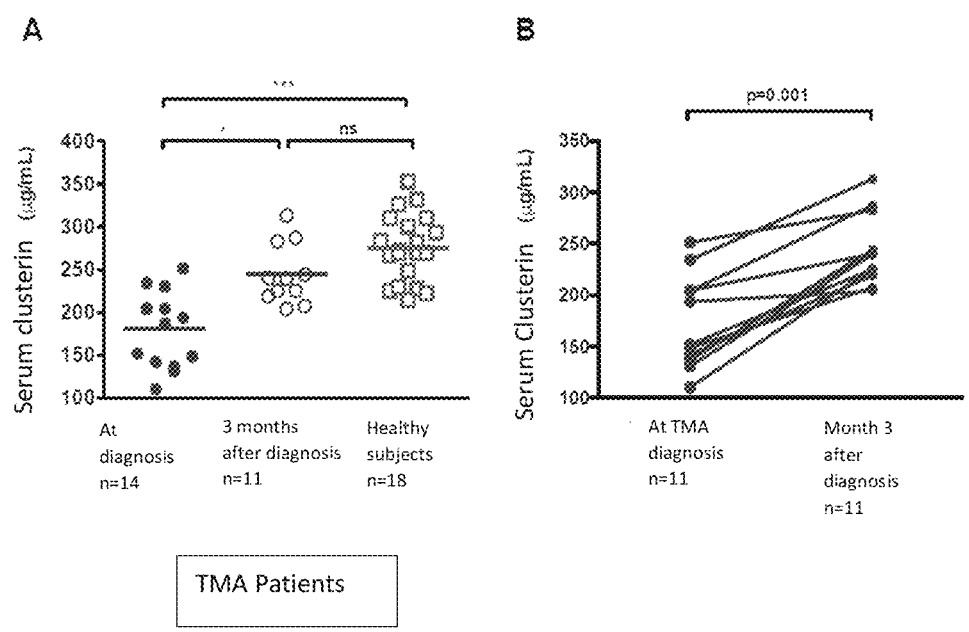
FIG. 4 represents the assaying of serum clusterin, in μg/ml, in patients suffering from TMA and healthy patients. (A) The serum clusterin is measured in healthy patients (squares) and TMA patients either at the beginning of the TMA (solid circles) or 3 months after diagnosis (empty circles). (B) The change in serum clusterin in TMA patients at diagnosis (points on the left) and 3 months after diagnosis (points on the right). Each point represents one patient. The statistical analysis was carried out by means of nonparametric tests.
Figure 5:
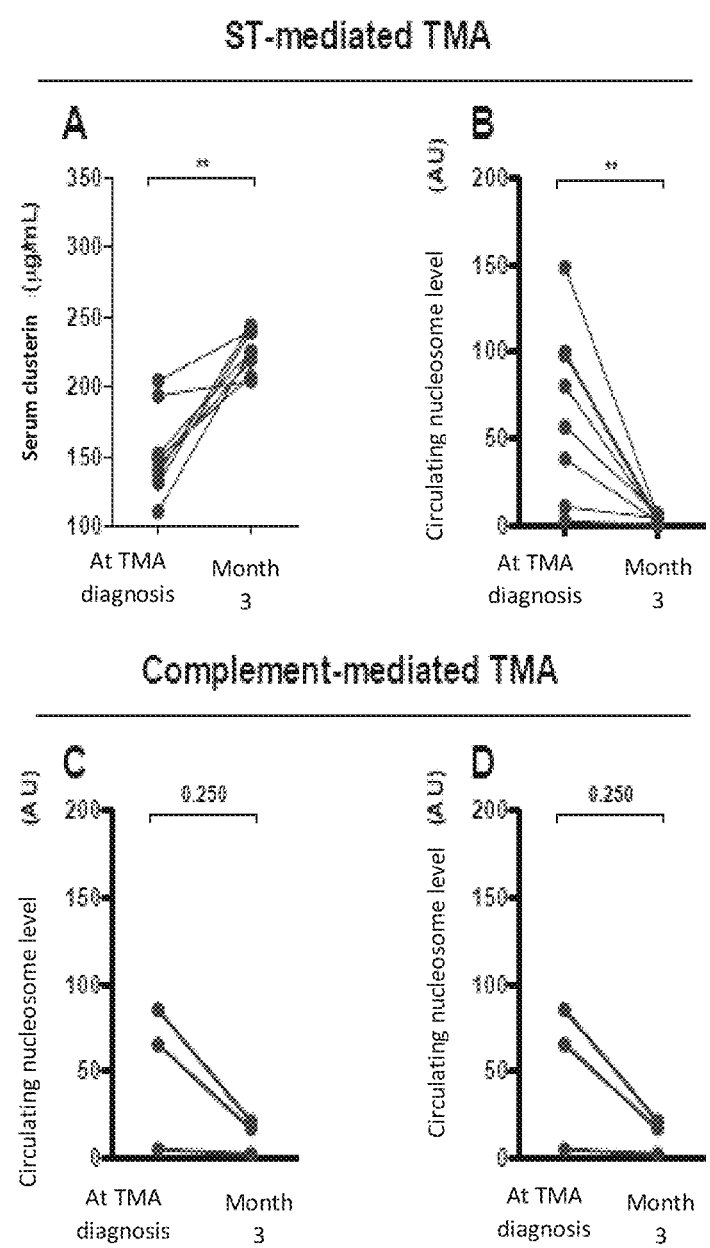
FIG. 5 represents (A) for the patients suffering from typical HUS, the assaying of serum clusterin in μg/ml, at TMA diagnosis (left) and after 3 months of treatment (right) with Eculizumab (Soliris); (B) for the patients suffering from typical HUS, the circulating nucleosomes level (AU) at TMA diagnosis (left) and after 3 months of treatment (right) with Eculizumab (Solids). The ST-mediated TMA patients (typical HUS) were treated uniformly with Eculizumab (Soliris) according to the same treatment scheme. (C) and (D) for the patients suffering from complement-mediated TMA, the circulating nucleosome level (AU) at TMA diagnosis (left) and after 3 months of treatment (right) with Eculizumab (Solids); the complement-mediated TMA patients were treated variably according to the clinical context.
Figure 6:
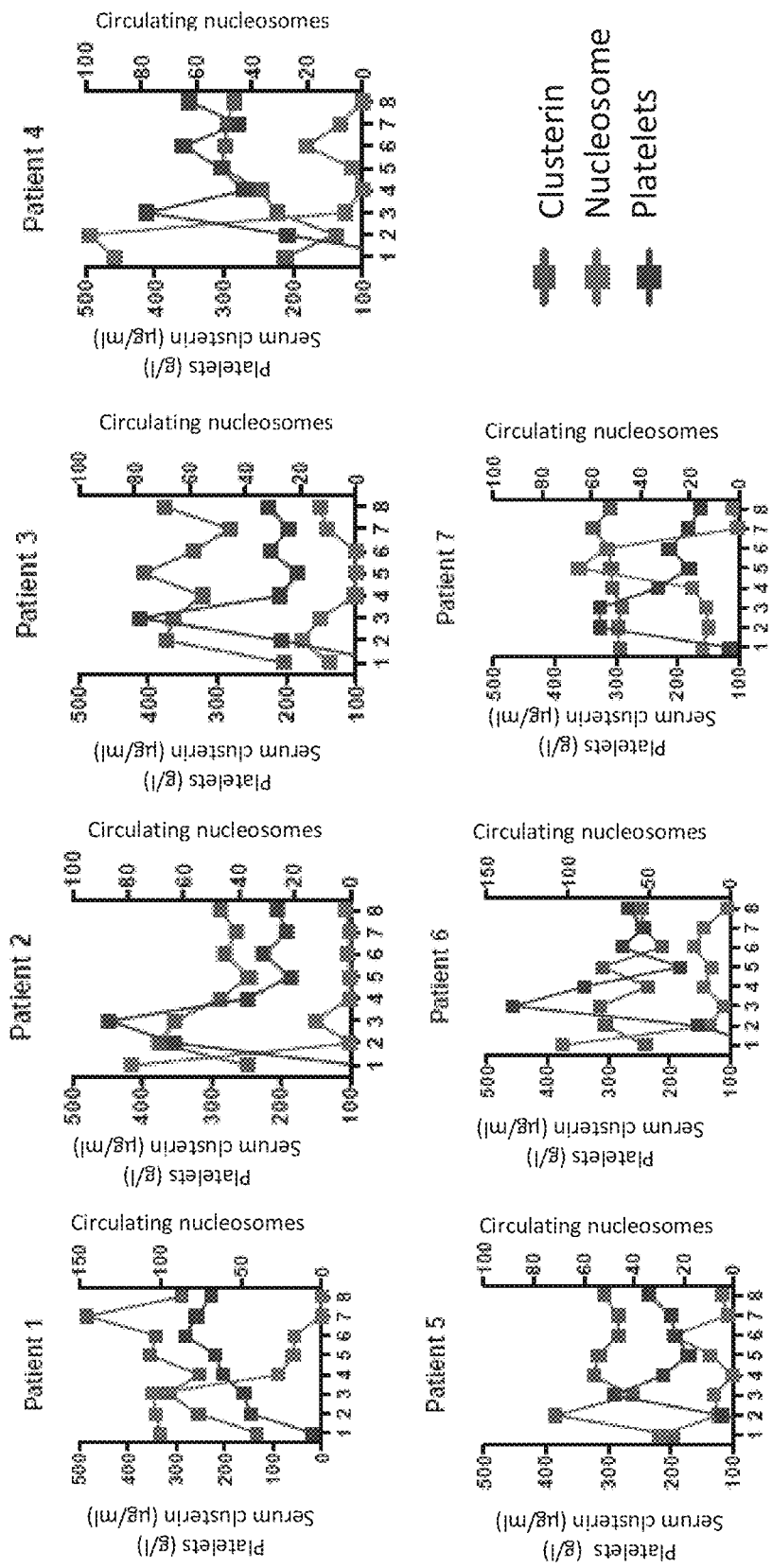
FIG. 6 represents the concentration of platelets, in g/l (dark gray), of serum clusterin in μg/ml (light gray) and of circulating nucleosomes in AU (medium gray), in 7 patients suffering from TMA, from the $1^{st}$ to the $8^{th}$ Eculizumab injection of the patients (tHUS, n=7). The serum clusterin, the circulating nucleosomes and the platelet concentration were measured just before each Eculizumab injection. Eculizumab was injected repeatedly every 2 weeks. The $8^{th}$ injection took place after an average period of 2 months from the diagnosis of a HUS.
Figure 7:
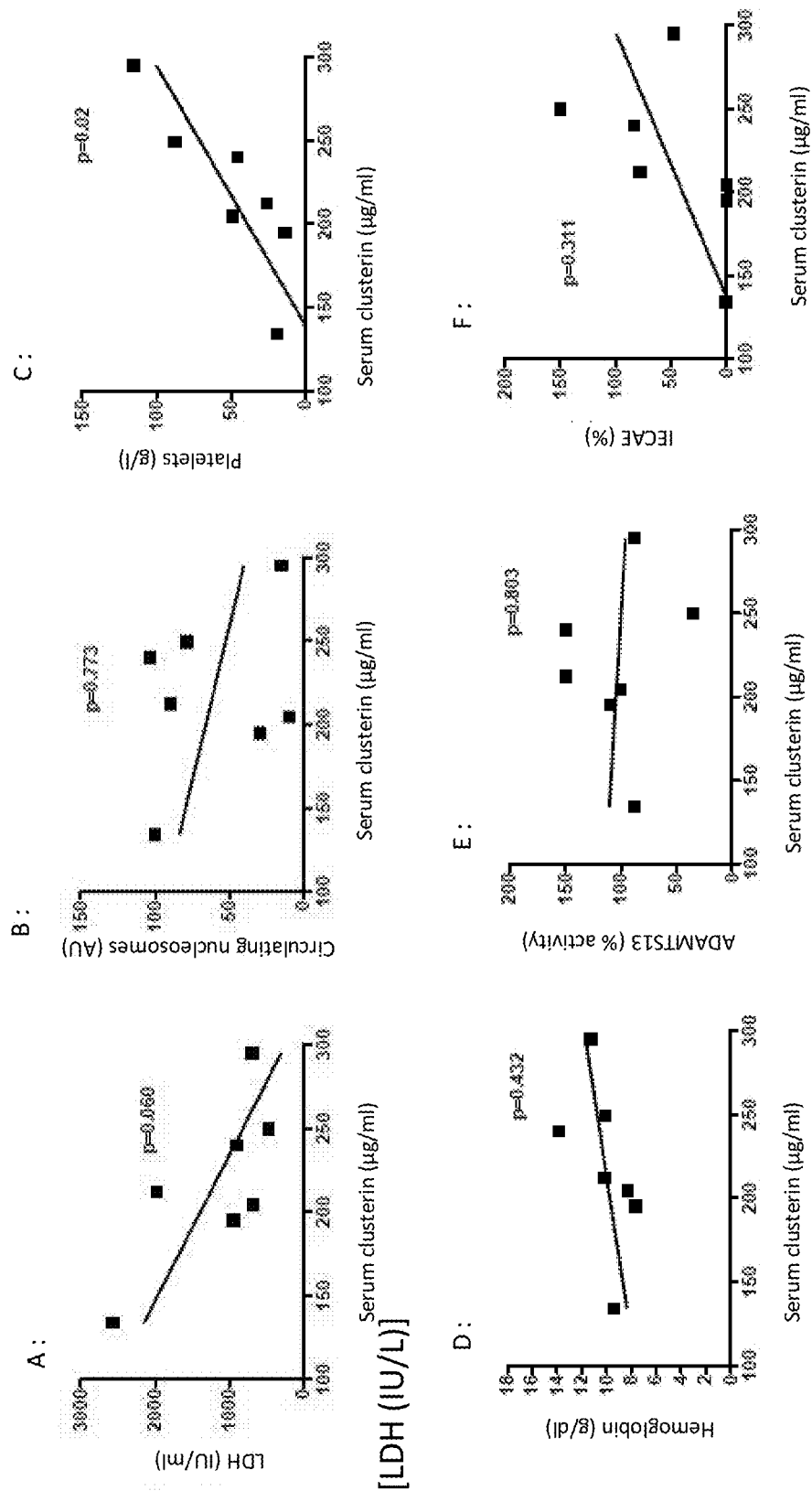
FIG. 7 represents A: the LDH concentration (IU/ml), B: the circulating nucleosome concentration (AU), C: the platelet concentration (g/l), D: the hemoglobin concentration (g/dl), E: the ADAMTS13 concentration (% activity) and F: the percentage IECAE (an arbitrary unit measuring the functional activity of the common terminal complement pathway by ELISA assay, the company Diasorin) as a function of the serum clusterin concentration (μg/ml) in a patient at the time of diagnosis of a tHUS (shiga toxin-mediated HUS).
Figure 8:
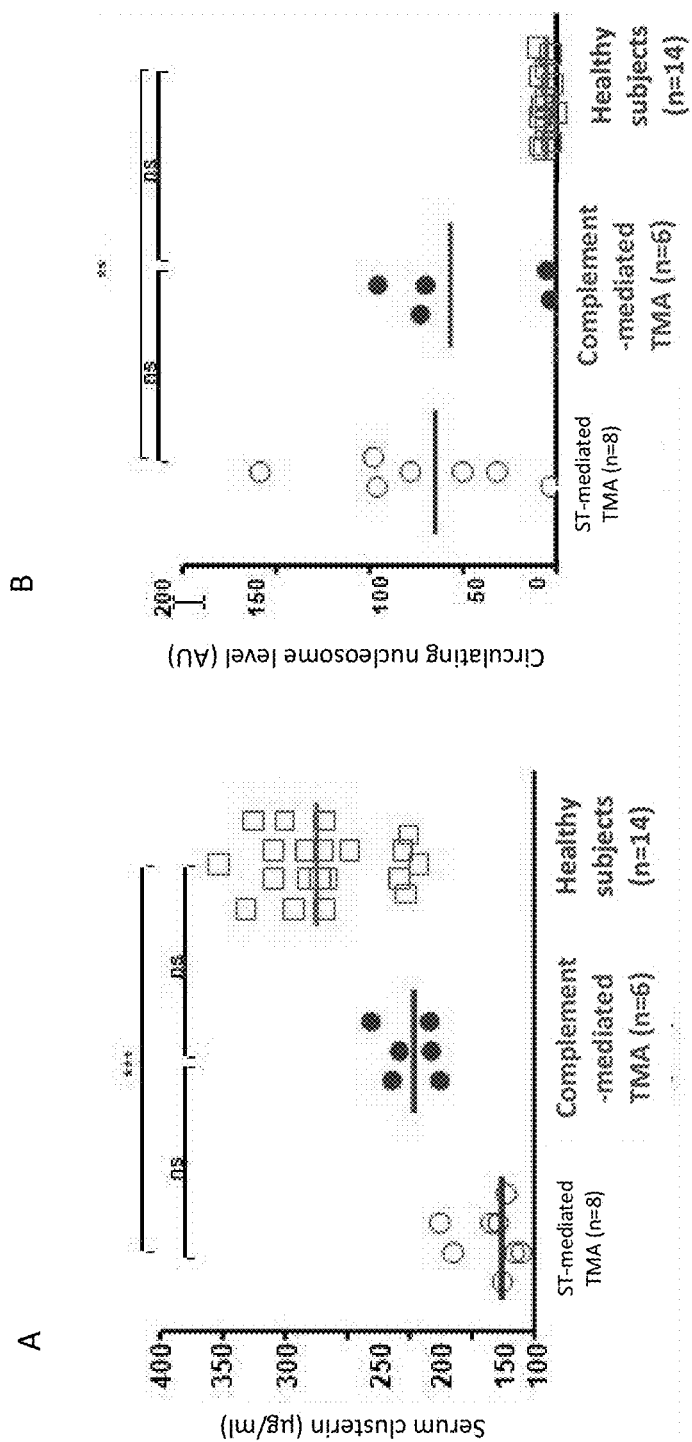
FIG. 8 represents (A): the assaying of the serum clusterin, in μg/ml, in patients suffering from shiga toxin-mediated TMA, tHUS (n=8), patients suffering from complement-mediated TMA, aHUS (n=6) and healthy subjects (n=14); (B) the circulating nucleosome level, in AU, in patients suffering from shiga toxin-mediated TMA (n=8), patients suffering from complement-mediated TMA (n=6) and healthy subjects (n=14).

The results are shown in FIG. 4.

Example 4: The Clusterin Deficiency is Observed in Various Types of TMA

An assay of the clusterin, the histones and a marker for activation of the common terminal pathway in the serum is carried out in patients suffering from typical HUS (20 cases) or atypical HUS (10 cases), from TTP (30 cases) and/or from HELLP syndrome (50 cases), at diagnosis and as follow up. These assays are carried out using commercial ELISA techniques.

The expected results make it possible to establish statistical associations and/or correlations with the main patient follow-up biological criteria (platelet level, LDH, haptoglobin level, markers for renal damage (creatininemia, albuminuria/creatininuria, etc.) or markers for extrarenal damage if applicable (troponin, ASAT/ALAT, gammaGT etc.).

Example 5: Clusterin is an Endothelial Cytoprotector in TMA Syndromes

Microvascular endothelial cells are incubated in the presence of sera from patients suffering from HUS, from TTP or from HELLP syndrome with or without addition of recombinant clusterin (target dose 25 µg/ml) for 2 h, 6 h or 24 h. The analysis of cell death (apoptotic or necrotic cell death) is carried out by flow cytometry labeling (annexin-5, propidium iodide).

It is expected that the histones and nucleosomes circulating in the sera of patients suffering from TMA cause endothelial lesions, and that the addition of clusterin protects the endothelial cells against death induced by these toxic elements.

Example 6: Clusterin Demonstrates an In Vivo Effect in a Murine Model of Typical HUS Two types of analyses are carried out.

1) Study of STX-induced renal toxicity in C57BL/6J mice wherein the clusterin gene has been knocked out (KO Clu) so as to demonstrate a worsening of the renal toxicity and of the biological markers for HUS (thrombocytopenia, anemia) in the absence of clusterin In a first part of the experiments, a sublethal dose is desired in order to monitor more accurately the HUS markers, namely anemia, thrombocytopenia and renal failure. The doses of 625 pg/g, 300 pg/g and 100 pg/g are tested on wild-type animals (10 mice per dose, plus 10 control mice). The mice are weighed daily, and the weight is used as an indicator of toxicity since, in the murine model, weight loss correlates with the disease.

Once the dose has been established, WT mice and clusterin-KO mice are injected intraperitoneally with the chosen dose of STX or with PBS and are then monitored by taking a blood sample on which a complete blood count is carried out. Hemoglobin is assayed in parallel in order to calculate an anemia index. The serum is also analyzed for renal failure markers (creatinine and cystatin). The kidneys are removed in order to analyze the deposits of C3 protein, which is a marker for renal lesions.

2) Study of the protective and therapeutic role of clusterin in TMA in a murine model of HUS in normal C57BL/6J mice (not clusterin deficient)

The WT mice are injected intraperitoneally with the chosen dose of STX or with PBS. The mice are treated with regular injections of recombinant murine clusterin (1 mg/kg). Monitoring is carried out by taking a blood sample on which a complete blood count is carried out. Hemoglobin is assayed in parallel in order to calculate an anemia index. The serum is also analyzed for the renal failure markers (creatinine and cystatin). The kidneys are removed in order to analyze the deposits of C3 protein, which is a marker for renal lesions.

It is expected that:

there is a correlation between the absence of clusterin and the worsening of renal toxicity and of the biological markers of HUS (thrombocytopenia, anemia)

the results make it possible to demonstrate the non-redundant role of clusterin in controlling shiga toxin-induced toxicity in a murine model the results demonstrate a protective and therapeutic role of clusterin in TMA in a murine model of HUS and demonstrate an improvement in renal function and in the hemolysis and thrombocytopenia parameters of the mice receiving supplementation compared with the control group.

The invention claimed is:

1. A method of treating a thrombotic microangiopathy in a subject, comprising detecting a deficiency in serum clusterin level in said subject and treating the thrombotic microangiopathy by increasing serum clusterin levels in said subject by administering to the subject a therapeutically effective amount of a pharmaceutical composition wherein the composition consists of clusterin as an active agent, wherein the pharmaceutical composition excludes a von Willebrand factor-cleaving protease.

2. The method of claim 1, wherein said clusterin is a human clusterin of sequence SEQ ID No.: 1.

3. The method of claim 1, wherein said clusterin has a peptide sequence which has at least 90% identity with the sequence SEQ ID No.: 1.

4. The method of claim 1, wherein said clusterin is a recombinant clusterin, a plasma clusterin, or a synthetic clusterin.

5. The method of claim 1, wherein the thrombotic microangiopathy is thrombotic thrombocytopeniaurpura (TTP), hemolytic uremic syndrome (HUS) associated or not associated with bacteria, HELLP syndrome, or a secondary thrombotic microangiopathy.

6. The method of claim 1, comprising oral or parenteral administration of said clusterin.

7. The method of claim 6, wherein said parenteral administration is intravenous administration, intramuscular administration, or subcutaneous administration.

* * * * *